United States Patent
Schubert

(10) Patent No.: US 6,924,115 B2
(45) Date of Patent: *Aug. 2, 2005

(54) PROCESS FOR IDENTIFYING CELL-SPECIFIC TARGET STRUCTURES

(76) Inventor: Walter Schubert, Am Mühlengrund 9, D-39175 Biederitz (DE)

( * ) Notice: Subject to any disclaimer, the term of this patent is extended or adjusted under 35 U.S.C. 154(b) by 324 days.

This patent is subject to a terminal disclaimer.

(21) Appl. No.: 09/808,224

(22) Filed: Mar. 14, 2001

(65) Prior Publication Data

US 2001/0039023 A1 Nov. 8, 2001

(30) Foreign Application Priority Data

Mar. 24, 2000 (DE) .......................................... 100 14 685

(51) Int. Cl.⁷ ...................... G01N 33/567; G01N 33/53; G01N 35/00
(52) U.S. Cl. ........................... 435/7.21; 435/7; 435/7.2; 435/43
(58) Field of Search ....................... 435/7.21, 7; 436/43

(56) References Cited

U.S. PATENT DOCUMENTS 6,150,173 A * 11/2000 Schubert ..................... 436/43

FOREIGN PATENT DOCUMENTS

DE 197 09 348 3/1997
EP 810 428 A3 12/1997

* cited by examiner

Primary Examiner—Rodney P Swartz
Assistant Examiner—Khatol S. Shahnan-Shah
(74) Attorney, Agent, or Firm—Weingarten, Schurgin, Gagnebin & Lebovici LLP

(57) ABSTRACT

This invention relates to a process for identifying cell-specific target structures. The process comprises automatically depositing a reagent solution that includes at least one marker molecule on an object which contains cells and/or cell membranes originating from a cell or tissue sample, allowing the reagent solution to react and automatically detecting at least one marker pattern of the object labeled with the reagent solution, removing said reagent solution, combining detected marker patterns, repeating the process with at least one further object, determining at least one difference in the objects, identifying at least one reagent solution causing the at least one difference, selecting molecules or molecular complexes from a homogenate of cells and/or cell membranes, and biochemically characterizing these molecules or molecular complexes.

15 Claims, No Drawings

PROCESS FOR IDENTIFYING CELL-SPECIFIC TARGET STRUCTURES

CROSS REFERENCE TO RELATED APPLICATION

This application claims priority to German Patent Application No. 100 14 685.6, filed Mar. 24, 2000.

DESCRIPTION

The invention relates to a process for identifying cell-specific target structures.

Identifying cell-specific target structures is crucial for elucidating cell-to-cell interactions which may cause countless effects within an organism. Especially, knowing disease-specific target structures is a decisive prerequisite for developing effective drugs which at the same time only have few side effects.

It is known from the prior art that immune cells (lymphocytes) will express specific combinations of proteins, also referred to as protein combination patterns or, in short, PCP, which are responsible for binding to endothelioid cells of the blood vessels in the brain and in muscle tissue. Other protein combinations, however, will not result in any binding to such endothelioid cells. Surprisingly, these specific combinations are inter-individually consistent, always exhibiting the same binding functions. Consequently, the specific protein combination patterns seem to be an inter-individually consistent lymphocyte binding code of the cell surface for organ-specific endothelioid cell surfaces which represents a cell-specific target structure. Cell-specific target structures may thus exhibit quite specific protein combination patterns.

The surfaces of invasive tumor cells also exhibit specific protein combination patterns which will cause a well-aimed, i.e. organ-selective invasive behavior. For this reason, such protein combination patterns constitute target structures for possible drugs.

However, an inevitable prerequisite for the development of such highly selective drugs is the knowledge of the molecular compositions of these target structures.

Disclosed in the prior art are processes for identifying target structures which are based on an analysis of gene expression profiles of sick tissues or cells as compared to gene expression profiles of healthy tissues or cells, with both protein expression profiles and expression profiles of the messenger ribonucleic acid (mRNA) being intended to provide information on the appearance of new proteins, mal-controlled or abnormally modified proteins in sick tissues or cells (e.g. in: F. Lottspeich/H. Zorbas; Bioanalytik; Spektrum Analytischer Verlag; Heidelberg, 1998).

However, these processes are all used with cell homogenates which are usually based on thousands or millions of cells since it is only possible by means of these multitudes of cells to create expression profiles of the above mentioned kind. In the cell homogenates, the cells are contained in broken open form so as to allow the proteins or mRNA molecules to be extracted and separated by means of biochemical processes.

One disadvantage of these prior art processes is, however, that they are not suitable for identifying protein combination patterns since the individual protein components of one such protein combination pattern will be completely separated by the generation of cell homogenates and by the subsequent extraction steps, thus losing the relevant information concerning their cellular and tissue-topological location. Furthermore, destroying the cellular compartments will make it impossible to obtain information regarding the protein combinations within these cellular compartments and their relative topological interrelationship.

Moreover, another shortcoming of the prior art processes is that they do not allow analyses to be performed on an individual cell level, which makes it impossible to tell in which way the individual cells differ in their protein combination patterns. Besides, proteins which are only present in a small amount will not be detected by the prior art processes. This is especially true for proteins or specific protein combinations which e.g. only exist in few, yet pathogenic, disease-specific cells.

Another disadvantage of the prior art processes is that the steps for preparing the tissue or the cells, from their withdrawal or collection to the step of isolating or separating proteins, may be subjected to a vast number of variable external influences which are hard to control and standardize.

It is, therefore, the object of the present invention to provide a process of the above mentioned kind which will allow the identification of cell-specific combination patterns, and which will overcome the above listed shortcomings of the prior art.

This object is accomplished by an inventive process for identifying cell-specific target structures, comprising the following steps: (a) automatically depositing a reagent solution Y1 that includes at least one marker molecule on an object X1 which contains cells and/or cell membranes originating from a cell or tissue sample; (b) allowing the reagent solution Y1 to react, and automatically detecting at least one marker pattern of the object X1 labeled with the reagent solution Y1; (c) removing said reagent solution Y1 before or after detecting the marker pattern, and repeating steps (a) and (b) with further reagent solutions Yn (n=2, 3, ..., N) each containing said at least one marker molecule and/or at least another marker molecule; (d) combining the marker patterns detected in step (b) to give a complex molecular combination pattern of object X1; (e) repeating steps (a) to (d) with at least one further object Xn (n=2, 3, ..., N) containing other cells and/or other cell membranes that originate from a different cell or tissue sample; (f) determining at least one difference between the combination pattern of object X1 and that of object Xn; (g) identifying at least one reagent solution Y1 or Yn whose marker pattern causes the difference determined in step (f); and (h) selecting molecules or molecular complexes bound by at least the one marker molecule of the reagent solution Y1 or Yn identified in step (g) from a homogenate of cells and/or cell membranes originating from the cell or tissue sample of the object Xn differing as determined in step (f); and (i) biochemically characterizing the molecules or molecular complexes selected in step (h).

The process of the invention allows a comparative examination of the protein combination patterns of individual cells or cell membranes originating from different cell or tissue samples. In doing so, those marker molecules can be identified which bind to e.g. a certain protein combination pattern or to a certain area of such a protein combination pattern of a first object originating from a first tissue or cell sample, and which at the same time do not bind to a second object originating from a second tissue or cell sample. By means of these identified marker molecules, it will then be possible, using a sample portion of the first tissue and/or cell sample, to detect or select, and subsequently characterize, those molecular regions (molecules or molecular complexes) of the protein combination pattern which are bound by the identified marker molecules. This will allow the detection of the molecular composition of a protein combination pattern, the arrangement of the molecules within said protein combination pattern as well as the arrangement of the protein combination pattern within a tissue or a cell.

According to a particularly advantageous further development of the invention, the homogenate used in step (h) will be separated into individual homogenate ingredients by means of molecule or molecular complex separation processes, in particular protein separation processes, before step (h). This will extremely facilitate the selection of the molecules or molecular complexes from the homogenate.

In another advantageous further development of the process according to the invention, object X1 contains cells and/or cell membranes originating from a cell or tissue sample of a sick patient, and at least one other object Xn contains cells and/or cell membranes originating from a cell or tissue sample of a healthy test person. This will allow identification of disease-specific target structures or the respective protein combination patterns, and based on the knowledge of these disease-specific protein combination patterns, it will be possible to develop highly specific drugs, which will be virtually free of side effects owing to this very specificity.

In another advantageous further development of the invention, the process comprises the following parallel step: (x) preparing a protein expression profile each of a sample portion each of said cell or tissue samples from which cells and/or cell membranes will be used in objects X1 and Xn, and comparing the protein expression profile associated with object X1 with that associated with object Xn, which comparison will show at least one difference.

Furthermore, the process of the invention may comprise the following step, after step (x): (y) examining at least one protein and/or at least one protein modification causing the difference determined in step (x), as to whether it binds to said at least one marker molecule of reagent solution Y1 or Yn identified in step (g). This will allow a determination of whether the differences detected by comparing the protein expression profiles are process-related artefacts (see above) or whether they actually constitute significant differences since they were also detected in the process according to the invention. The process of the invention can thus also be used as an important supplement to the processes already known.

In yet another, particularly advantageous further development of the invention, at least one marker molecule used in step (a) and/or step (c) binds at least one protein and/or at least one protein modification causing the difference determined in step (x). Using known processes, antibodies or ligands may e.g. be developed which will bind proteins or protein modifications which were identified as target structure regions by comparing protein expression profiles. Using these antibodies or ligands in the process of the invention will allow an examination as to whether or not the proteins determined by comparing protein expression profiles will create protein combination patterns.

Furthermore, at least one marker molecule used in step (a) and/or in step (c) may be fluorochrome-conjugated. Such fluorescence labeling will make a marker molecule especially easy to detect.

Moreover, at least one marker molecule used in step (a) and/or in step (c) may be an antibody, which antibody may be taken from an antibody library, which antibody library may be of the naive or of the non-naive type. The so-called naive antibody library is a library whose antibodies do not exhibit any known specificity, whereas the antibodies of the non-naive antibody library will recognize known molecules such as proteins or glyco-proteins. Use of a non-naive library will thus provide immediate information, right from the very identification of an antibody, as to which molecule(s) said antibody will bind.

Furthermore, at least one marker molecule used in step (a) and/or in step (c) may be a ligand. Said ligand may be taken from a ligand library which library may be of the naive or the non-naive type. The terms "naive" and "non-naive" are to be understood on the analogy of the above explanations.

After removing the reagent solution in step (c), a rinsing step may follow in which a rinsing solution is deposited on object X1 and removed again after a certain period of time. This will prevent a newly deposited reagent solution from being contaminated by a previously applied reagent solution.

Advantageously, step (d) may be performed by computer-aided image overlay.

The process may comprise randomly repeatable bleaching cycles, in particular after step (b). Such bleaching cycles will prevent already detected markers from being detected again in a subsequent procedural step.

Further details, features and advantages of the invention may be gathered from the description, which follows, of an embodiment.

In the embodiment, a tissue or cell sample will be divided into two sample portions. The first sample portion will serve as starting material for producing a homogenate for biochemically characterizing proteins according to the known processes. In particular processes such as 2D gel electrophoresis will be used for preparing protein expression profiles.

The second sample portion will be used for making tissue sections or cell preparations with intact cells. Should the second sample portion be a tissue block, then a tissue section thereof will be made. However, if it is cells in a suspension, these cells will be applied in intact form onto a surface, in particular a specimen slide. The first object obtained in this way will be subjected to the following automated procedural steps:

1. Taking up a first reagent solution Y1 with one or plural fluorochrome-conjugated antibodies of a non-naive antibody library;
2. pipetting said reagent solution Y1 onto the first object;
3. incubating said object with this solution Y1 at a certain temperature, especially room temperature;
4. removing said reagent solution;
5. dropping a rinsing solution onto it once or plural times, and subsequently removing said rinsing solution;
6. applying a buffer solution to said first object;
7. detecting a fluorescence distribution pattern, with selective fluorescence recording filters being used for taking the pictures if plural fluorochromes are used. In this step, it will be determined whether and where the antibody/antibodies in the sample show binding signals. Positive and negative signals will likewise be digitally recorded for each image point or site point of the cells or the tissue of the first object;
8. pipetting a further rinsing solution thereonto;
9. bleaching the sample by means of fluorescence excitation, which bleaching step will be terminated once no fluorescence can be detected anymore;
10. removing said further rinsing solution;
11. taking up a second reagent solution Y2 with one or plural likewise fluorochrome-conjugated antibodies of a different or the same antibody library;
12. pipetting said reagent solution Y2 onto the first object.

This process is continued by repeating steps 1 to 10, with the reagent solutions Y3, Y4, Y5, . . . , Yn being used which may contain antibodies or ligands of non-naive or naive libraries. In this manner, one and the same object may be examined with a completely naive library, or a completely non-naive library, or a mixed type, non-naive and naive library.

Each of these process cycles (steps 1 through 10) will be terminated by recording a corresponding phase contrast image or differential interference contrast image.

Based on the marker patterns each recorded in step 7, the existing signal combinations and the non-existing signal combinations which—in total—will give a combination pattern, will be determined by means of computer-aided image overlay.

This combination pattern determined for the first object will be compared with other combination patterns of other samples or test persons, cells or states or diseases which were analyzed with the same reagent solutions according to the same standardized procedural steps as set out above.

Should this comparison produce unique signal combinations specific for the sample examined, or should it produce the signal combinations specific for a state, a cell type, a disease or a function, these signal combinations will be based on specific, i.e. selective molecular interactions, and will thus characterize said state, disease, function or cell type. It will then be possible to associate the respective antibodies or ligands with the signal combinations detected.

The antibodies and/or ligands filtered out in this way will then be used for "catching" those proteins, glyco-proteins or other carbohydrate structures within the first sample portion that are capable of specifically binding these ligands or antibodies. For this purpose, the processes known in biochemical analysis methods will be used. The molecules thus found may be individual molecular species or complexes of different molecular species. In either case, they constitute highly specific target structures, in particular for developing drugs.

What is claimed is:

1. A process for identifying cell-specific target structures, the process comprising the following steps:
   (a) automatically depositing a reagent solution Y1 that includes at least one marker molecule on an object X1 which contains cells and/or cell membranes originating from a cell or tissue sample;
   (b) allowing the reagent solution Y1 to react, and automatically detecting at least one marker pattern of the object X1 labeled with the reagent solution Y1;
   (c) removing said reagent solution Y1 before or after detecting the marker pattern, and repeating steps (a) and (b) with further reagent solutions Yn (n=2, 3, . . . , N) each containing said at least one marker molecule, at least another marker molecule; or both;
   (d) combining the marker patterns detected in step (b) to give a complex molecular combination pattern of object X1;
   (e) repeating steps (a) to (d) with at least one further object Xn (n=2, 3, . . . , N) containing other cells and/or other cell membranes that originate from a different cell or tissue sample;
   (f) determining at least one difference between the combination pattern of object X1 and that of object Xn;
   (g) identifying at least one reagent solution Y1 or Yn whose marker pattern causes the difference determined in step (f);
   (h) selecting molecules or molecular complexes bound by at least the one marker molecule of the reagent solution Y1 or Yn identified in step (g) from a homogenate of cells and/or cell membranes originating from the cell or tissue sample of the object Xn differing as determined in step (f); and
   (i) biochemically characterizing the molecules or molecular complexes selected in step (h).

2. The process as claimed in claim 1 wherein the homogenate used in step (h) will be separated into individual homogenate ingredients by means of molecule or a molecular complex separation processes, prior to step (h).

3. The process as claimed in claim 1 wherein said object X1 exhibits cells and/or cell membranes originating from a cell or tissue sample of a sick patient, and wherein at least one other object Xn exhibits cells and/or cell membranes originating from a cell or tissue sample of a healthy test person.

4. The process as claimed in claim 1 wherein said process comprises the following parallel step:
   (x) preparing a protein expression profile each of a sample portion each of said cell or tissue samples from which cells and/or cell membranes will be used in objects X1 and Xn, and comparing the protein expression profile to be associated with object X1 with that to be associated with object Xn, which comparison will show at least one difference.

5. The process as claimed in claim 4 wherein said process further comprises the step:
   (y) examining at least one protein and/or at least one protein modification causing the difference detected in step (x) as to whether said protein binds to at least one marker molecule of the reagent solution Y1 or Yn identified in step (g).

6. The process as claimed in claim 4 wherein at least one marker molecule used in step (a) and/or step (c) binds at least one protein and/or at least one protein modification causing the difference detected in step (x).

7. The process as claimed in claim 1 wherein at least one marker molecule used in step (a) and/or step (c) is fluorochrome-conjugated.

8. The process as claimed in claim 1 wherein at least one marker molecule used in step (a) and/or step (c) is an antibody.

9. The process as claimed in claim 8 wherein said antibody is taken from an antibody library, said antibody library being of the naive or of the non-naive type.

10. The process as claimed in claim 1 wherein at least one marker molecule used in step (a) and/or step (c) is a ligand.

11. The process as claimed in claim 10 wherein said ligand is taken from a ligand library, said ligand library being of the naive or of the non-naive type.

12. The process as claimed in claim 1 wherein after removing the reagent solution according to step (c), a rinsing step follows in which a rinsing solution is deposited on object X1 and removed again after a certain period of time.

13. The process as claimed in claim 1 wherein step (d) is performed by means of computer-aided image overlay.

14. The process as claimed in claim 1 wherein the process comprises randomly repeatable bleaching cycles, in particular after step (b).

15. The process as claimed in claim 3 wherein:
   said process comprises the following parallel steps:
   (x) preparing a protein expression profile of a sample portion each of said cell or tissue samples from which cells and/or cell membranes will be used from objects X1 and Zn, and comparing the protein expression profile to be associated with object X1 with that to be associated with object Xn, which comparison will show at least one difference; and
   (y) examining at least one protein and/or at least one protein modification causing the difference detected in step (x) as to whether it binds to at least one marker molecule of the reagent solution Y1 or Yn identified in step (g), wherein at least one marker molecule used in step (a) and/or step (c) binds at least one protein and/or at least one protein modification causing the difference detected in step (x);

at least one marker molecule used in step (a) and/or step (c) is fluorochrome-conjugated;

at least one marker molecule used in step (a) and/or step (c) is an antibody, said antibody is taken from an antibody library, said antibody library being of the naive or of the non-naive type;

at least one marker molecule used in step (a) and/or step (c) is a ligand, said ligand being taken from a ligand library, said ligand library being of the relative or of the non-naive type;

after removing the reagent solution according to step (c), a rinsing step follows in which a rinsing solution is deposited on object X1 and removed again after a certain period of time;

step (d) is performed by means of computer-aided image overlay; and the process comprises randomly repeatable bleaching cycles, in particular after step (b).

* * * * *

UNITED STATES PATENT AND TRADEMARK OFFICE
CERTIFICATE OF CORRECTION

| | | |
|---|---|---|
| PATENT NO. | : 6,924,115 B2 | Page 1 of 1 |
| APPLICATION NO. | : 09/808224 | |
| DATED | : August 2, 2005 | |
| INVENTOR(S) | : Walter Schubert | |

It is certified that error appears in the above-identified patent and that said Letters Patent is hereby corrected as shown below:

Title page (30), "100 14 685" should read --100 14 685.6--;

Column 6, claim 5, lines 22-23, "at least one protein and/or at least one protein modification" should read --at least one protein, at least one protein modification, or both--;

Column 6, claim 15, line 59, "Zn" should read --Xn--; and

Column 7, claim 15, line 9, "relative" should read --naive--.

Signed and Sealed this

Twelfth Day of December, 2006

JON W. DUDAS
*Director of the United States Patent and Trademark Office*

UNITED STATES PATENT AND TRADEMARK OFFICE
CERTIFICATE OF CORRECTION

| | |
|---|---|
| PATENT NO. | : 6,924,115 B2 |
| APPLICATION NO. | : 09/808224 |
| DATED | : August 2, 2005 |
| INVENTOR(S) | : Walter Schubert |

It is certified that error appears in the above-identified patent and that said Letters Patent is hereby corrected as shown below:

Column 6, claim 4, line 13, "profile each of a sample" should read --profile of a sample--.

Signed and Sealed this

Twenty-seventh Day of March, 2007

JON W. DUDAS
*Director of the United States Patent and Trademark Office*